(12) United States Patent
Bazin et al.

(10) Patent No.: US 10,906,022 B2
(45) Date of Patent: Feb. 2, 2021

(54) PHOTOCHEMISTRY DEVICE

(71) Applicant: HepatoChem, Inc., Beverly, MA (US)

(72) Inventors: Marc J. Bazin, Lincoln, MA (US);
Ryan S. Buzdygon, Salem, MA (US)

(73) Assignee: HepatoChem, Inc., Beverly, MA (US)

( * ) Notice: Subject to any disclaimer, the term of this patent is extended or adjusted under 35 U.S.C. 154(b) by 0 days.

(21) Appl. No.: 16/461,079

(22) PCT Filed: Nov. 21, 2017

(86) PCT No.: PCT/US2017/062866
§ 371 (c)(1),
(2) Date: May 15, 2019

(87) PCT Pub. No.: WO2018/098189
PCT Pub. Date: May 31, 2018

(65) Prior Publication Data
US 2019/0270065 A1    Sep. 5, 2019

Related U.S. Application Data

(60) Provisional application No. 62/425,199, filed on Nov. 22, 2016.

(51) Int. Cl.
*B01J 19/12*    (2006.01)
*B01J 19/00*    (2006.01)
*C07D 401/12*    (2006.01)

(52) U.S. Cl.
CPC ......... *B01J 19/123* (2013.01); *B01J 19/0013* (2013.01); *B01J 19/0046* (2013.01); *B01J 19/0066* (2013.01); *B01J 19/128* (2013.01); *C07D 401/12* (2013.01); *B01J 2219/00074* (2013.01); *B01J 2219/00308* (2013.01); *B01J 2219/00481* (2013.01);
(Continued)

(58) Field of Classification Search
None
See application file for complete search history.

(56) References Cited

U.S. PATENT DOCUMENTS

| 4,517,063 A | 5/1985 | Cirjak |
| 5,184,020 A | 2/1993 | Hearst et al. |

(Continued)

FOREIGN PATENT DOCUMENTS

| CN | 101234326 A | 8/2008 |
| CN | 104338501 A | 2/2015 |

(Continued)

OTHER PUBLICATIONS

International Application No. PCT/US2017/062866, entitled "Photochemistry Device," International Preliminary Report on Patentability, dated May 28, 2019.
(Continued)

*Primary Examiner* — Kishor Mayekar
(74) *Attorney, Agent, or Firm* — Hamilton, Brook, Smith & Reynolds, P.C.

(57) ABSTRACT

The invention consists of an assembly of a light (e.g., UV, visible, IR) source, a reaction vial holder and a photochemistry device that allows for conducting arrays of photochemical reaction conditions at room temperature with magnetic stirring. The photochemistry assembly is compatible with multiple reaction vial size holder.

14 Claims, 19 Drawing Sheets

(52) U.S. Cl.
CPC ............... *B01J 2219/00495* (2013.01); *B01J 2219/00704* (2013.01); *B01J 2219/0871* (2013.01); *B01J 2219/0877* (2013.01); *B01J 2219/0892* (2013.01); *B01J 2219/1203* (2013.01)

(56) References Cited

U.S. PATENT DOCUMENTS

| | | | | |
|---|---|---|---|---|
| 5,556,958 | A * | 9/1996 | Carroll | C07H 21/00 536/25.3 |
| 8,872,130 | B1 * | 10/2014 | Matthews | C02F 1/325 250/455.11 |
| 2003/0170141 | A1 * | 9/2003 | Hearst | B01L 7/00 422/22 |
| 2005/0182149 | A1 | 8/2005 | Crivello | |
| 2013/0327632 | A1 | 12/2013 | Hayashida | |

FOREIGN PATENT DOCUMENTS

| | | |
|---|---|---|
| WO | 91/06843 A1 | 5/1991 |
| WO | 2004/029567 A1 | 4/2004 |

OTHER PUBLICATIONS

Notification of Transmittal of International Search Report and the Written Opinion of the International Searching Authority, dated Jan. 25, 2018, and accompanying International Search Report and Written Opinion of the International Searching Authority, regarding International Application No. PCT/2017/062866, entitled "Photochemistry Device," filed Nov. 21, 2017.

Trident Labortek, Photochemical Reactors, http://www.tridentlabortek.com/photochemical_reactors.html (1 page), Mar. 11, 2016.

The Southern New England Ultraviolet Co., Merry Go-Round 400, https://rayonet.org/accessories.php?part=RMA-400, 7 pages), Sep. 13, 2016.

The Southern New England Ultraviolet Co., RMR-600 Photochemical Reactor, https://rayonet.org/reactors.php?part=RMR-600 (7 pages), Jan. 12, 2016.

Acceleration of Photocataylitic Reactions. Penn Optical Coatings (www.pennoc.com/acceleration-photocataylitic-reactions/), 2014.

Elliott, L et al., A Small-Footprint, High-Capacity Flow Reactor for UV Photochemical Synthesis on the Kilogram Scale. Organic Process Research & Development—American Chemical Society:1806-1811, 2016.

Le, C. et al., A General Small-Scale Reactor to Enable Standardization and Acceleration of Photocatalytic Reactions. ACS Central Science—American Chemical Society, 3:647-653, 2017.

Corning® Advanced—Flow™ Reaktoren. Corning (https://www.corning.com/emea/de/innovation/corning-emerging-innovations/advanced-flow-reactors.html), retrieve May 3, 2019.

G3 Photo Reactor brochure. Corning (www.corning.com/reactors), 2018.

Lab Photo Reactor brochure. Corning (www.corning.com/reactors), 2018.

Lumidox™ Photon Generator for Photoredox Applications (https://www.analytical-sales.com/Lumidox.html), retrieved May 3, 2019.

Luzchem. Luzchem Photoreactor Model LED-L16 (https://www.luzchem.com/ProductDetails.php?product_line_ID=1&product_ID=12), retrieved May 3, 2019.

Luzchem Photoreactor Model LED-L16 (specifications). Luzchem Research Inc. (www.luzchem.com).

Photoredox: charge of the LED brigade. Feature | Chemistry World (https://www.chemistryworld.com/features/photoredox-charge-of-the-led-brigade/3007944.article), retrieved May 3, 2019.

Photoredox. Merck-Macmillan Group (chemlabs.princeton.edu/macmillan/photoredox/), retrieved May 3, 2019.

\* cited by examiner

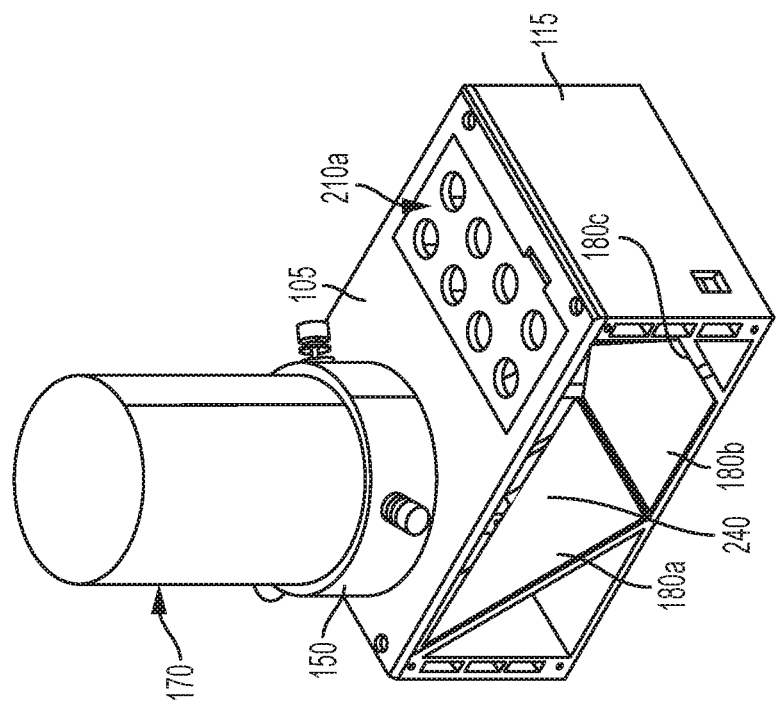
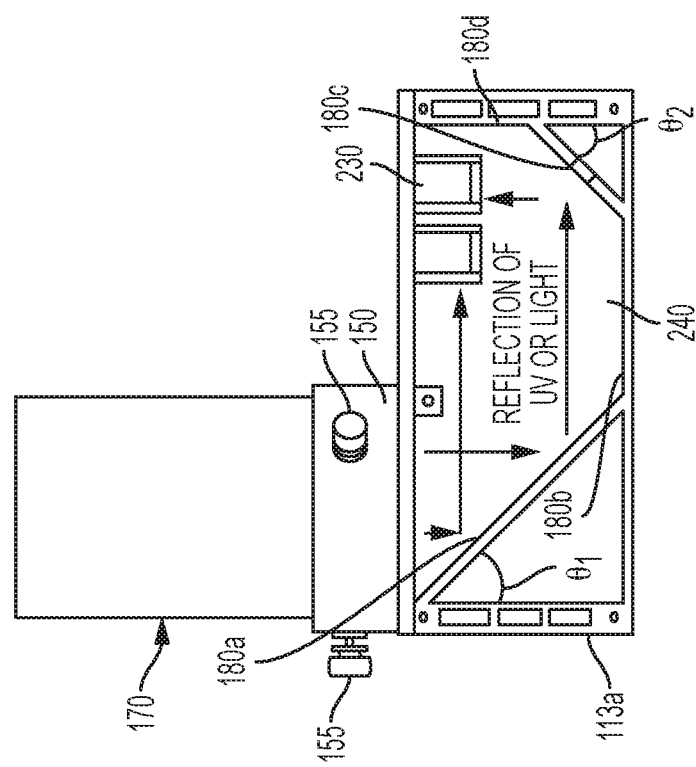
FIG. 3B
FIG. 3A

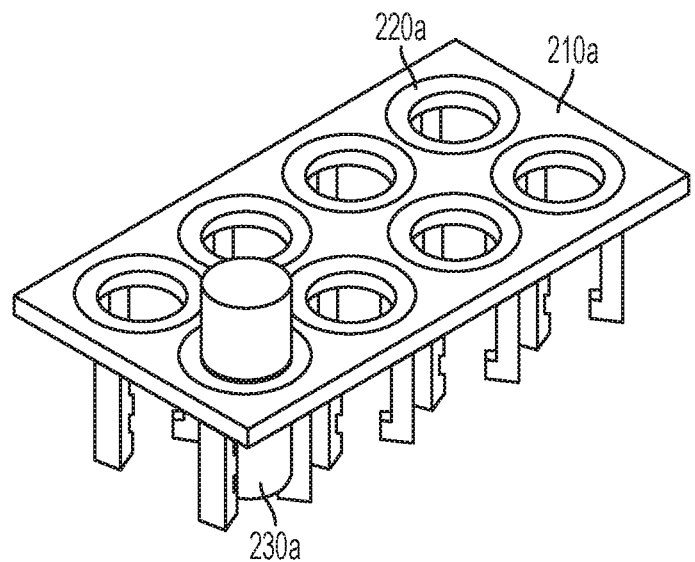
FIG. 5A
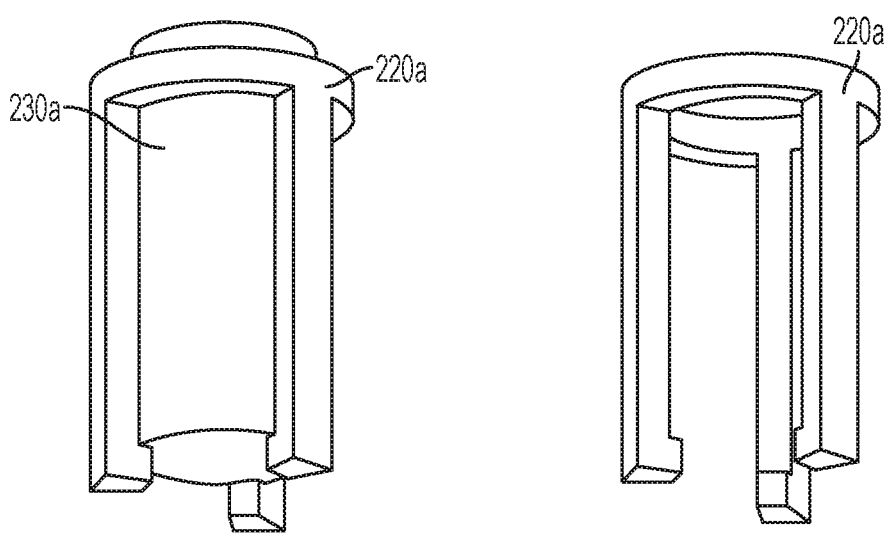
FIG. 5B
FIG. 5C

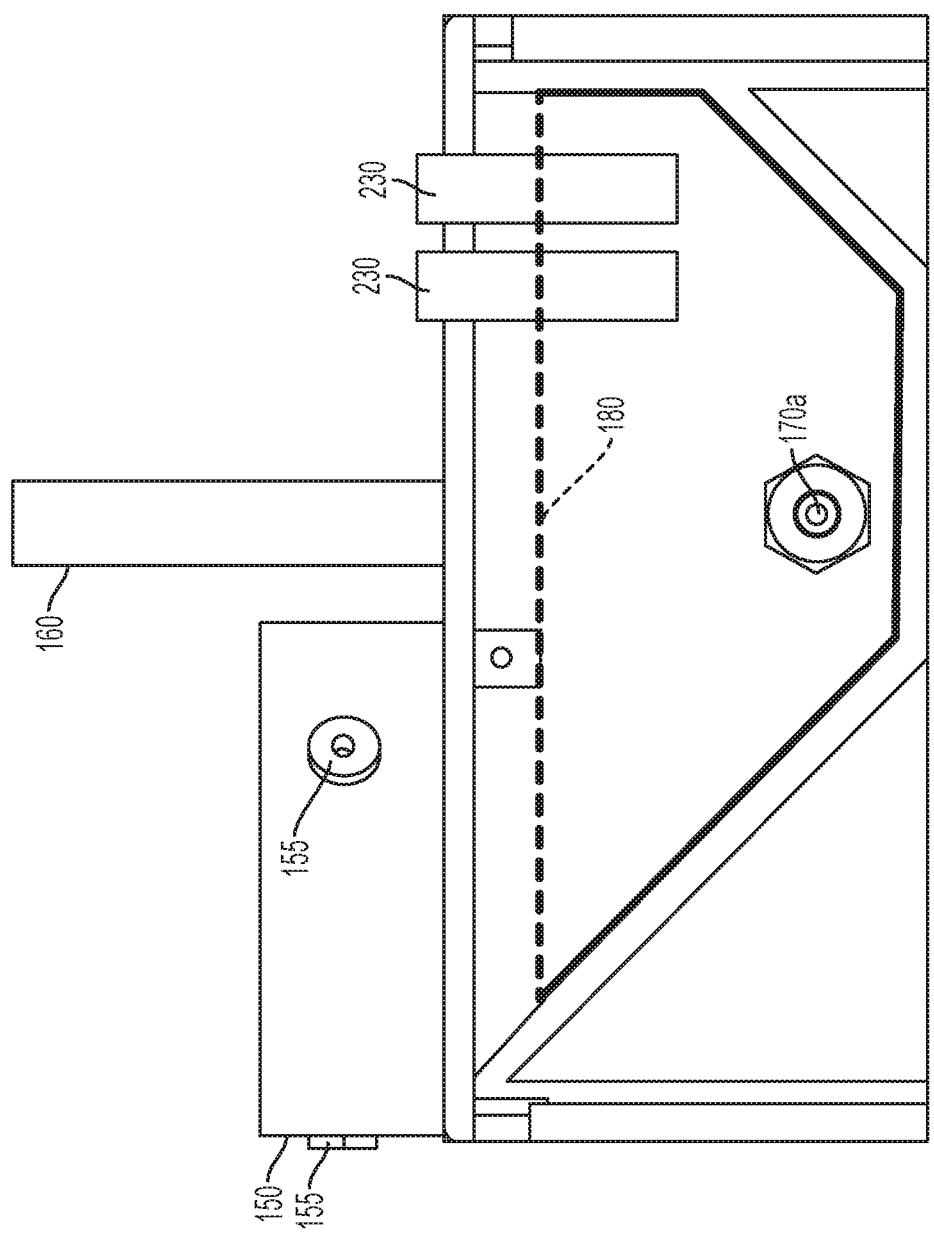

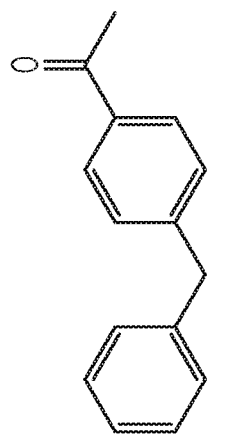
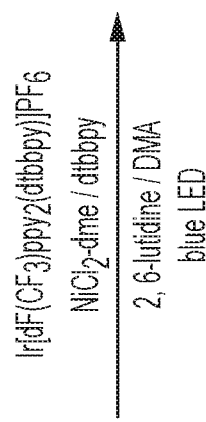
FIG. 16
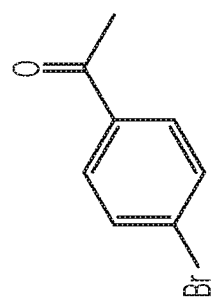
+
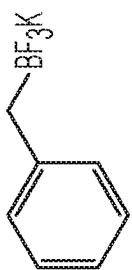

PHOTOCHEMISTRY DEVICE

RELATED APPLICATION

This application is the U.S. National Stage of International Application No. PCT/US2017/062866, filed Nov. 21, 2017, which designates the U.S., published in English, and claims the benefit of U.S. Provisional Application No. 62/425,199, filed Nov. 22, 2016. The entire teachings of the aforementioned applications are incorporated herein by reference.

BACKGROUND

Photochemical reactions are usually set up with a light (e.g., ultraviolet, visible, and infrared) source directed toward reaction vials. Devices or assemblies are needed in which to perform such photochemical reactions. When conducting scientific experiments, it is preferable to minimize or reduce factors that may impact the reaction.

If different reaction vials within an assembly for performing photochemical reactions are irradiated with different amounts of light, the results may be impacted because vials irradiated with more light may indicate a faster rate of reaction. Therefore, in many embodiments, the light should preferably irradiate the reaction vials uniformly.

If temperature fluctuates during the course of a reaction, it can be difficult to ascertain reaction rates or to meaningfully compare reaction rates. Therefore, the reaction vessels are preferably maintained at a constant temperature, frequently room temperature, in order to reduce undesired thermal effects. However, there are also instances where it is preferable to conduct reactions at an elevated temperature in order to probe the effect of reaction temperature on photochemical reactions.

Often, reactions are stirred to ensure homogenization of the reaction mixture. Therefore, the assembly preferably permits the reaction to be stirred, such as with a standard mixing plate.

Depending on the particular reaction being studied, it may be desirable to use reaction vials of differing sizes. Preferably, the assembly is capable of being used with reaction vials of differing sizes.

Thus, assemblies that provide the aforementioned features and functionality are needed.

SUMMARY OF THE INVENTION

The invention comprises an assembly for conducting a series of photochemical reactions. Use of the assemblies can facilitate simultaneous performance of a plurality of photochemical reactions.

Described herein is an assembly for performing one or more photochemical reactions. The assembly can include a housing. The housing defines an interior cavity having positioned therein one or more mirrors that reflect light from the light source towards the one or more reaction vials. The housing can include an opening for receiving a removable holder, an adaptor for receiving a light source, and ports for entry and exit of a fluid for adjusting the temperature of the reaction vials. The removable holder is capable of holding one or more reaction vials. The light source is exterior to the housing.

The assembly can include a handle affixed to the housing. The assembly can be secured by clamping the handle with a standard three-prong laboratory clamp.

A top face of the housing can be removable. One or more screws can couple a light source with the adaptor for receiving the light source. Different removable holders for reaction vials are adapted to receive reactions vials of different sizes. The removable holder for reaction vials can have openings to receive, for example, 2, 3, 8, or 32 reaction vials.

The housing can include two adaptors for receiving a light source. The housing can include two openings for receiving a removable holder. In some instances, the housing can include two adaptors for receiving a light source and two openings for receiving a removable holder.

In some embodiments, a first mirror is positioned such that the face of the mirror extends from a top corner of the interior cavity towards a bottom face of the house, and at an acute angle relative to a side wall, such that the mirror reflects light toward an opposing side wall.

In some embodiments, the fluid is a gas, and the ports are openings to permit the gas to flow into and out of the interior cavity. In some instances, the assembly can include a fan at one of the ports. The assembly can also include a cover parallel to and offset from one of the ports.

In some embodiments, the fluid is a liquid, and the ports are nozzles to permit the liquid to flow into and out of the interior cavity.

The holders can be supported by the window frame. The holders are designed to allow light through and facilitate the photochemical reaction.

The assemblies described herein can be used to conduct a series of experiments with an array of reagents, solvents and/or catalysts for photochemical reactions.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 3A is a front side view of an embodiment of an assembly of this invention for conducting photochemical reactions.

FIG. 3B is a front elevated view of an embodiment of an assembly of this invention for conducting photochemical reactions.

FIG. 5A is a front elevated view of an embodiment of a removable holder for reaction vials for use in an embodiment of this invention.

FIG. 5B is an enlarged view of an embodiment of an insert and reaction vial for use in an embodiment of this invention.

FIG. 5C is an enlarged view of an insert of use in an embodiment of this invention.

FIG. 6B shows mirrors and a fan inside the assembly.

FIG. 7A is a schematic of a front elevated view of an assembly set-up on a stirring plate. The light source is activated, and UV light is shining on the reaction vials. FIG. 7B is a schematic of a front elevated view of an assembly. FIG. 7C is a schematic of an elevated front view of an embodiment of an assembly for performing photochemical reactions. The photograph is annotated with arrows indicating the direction of air flow through the assembly.

FIG. 8A shows the embodiment with the top face attached, and FIG. 8B shows the embodiment without the top face.

FIG. 9 is a side view of the embodiment of FIGS. 8A-B.

FIG. 16 is a reaction for a photoredox cross-coupling reaction test.

DETAILED DESCRIPTION

Figure 1:
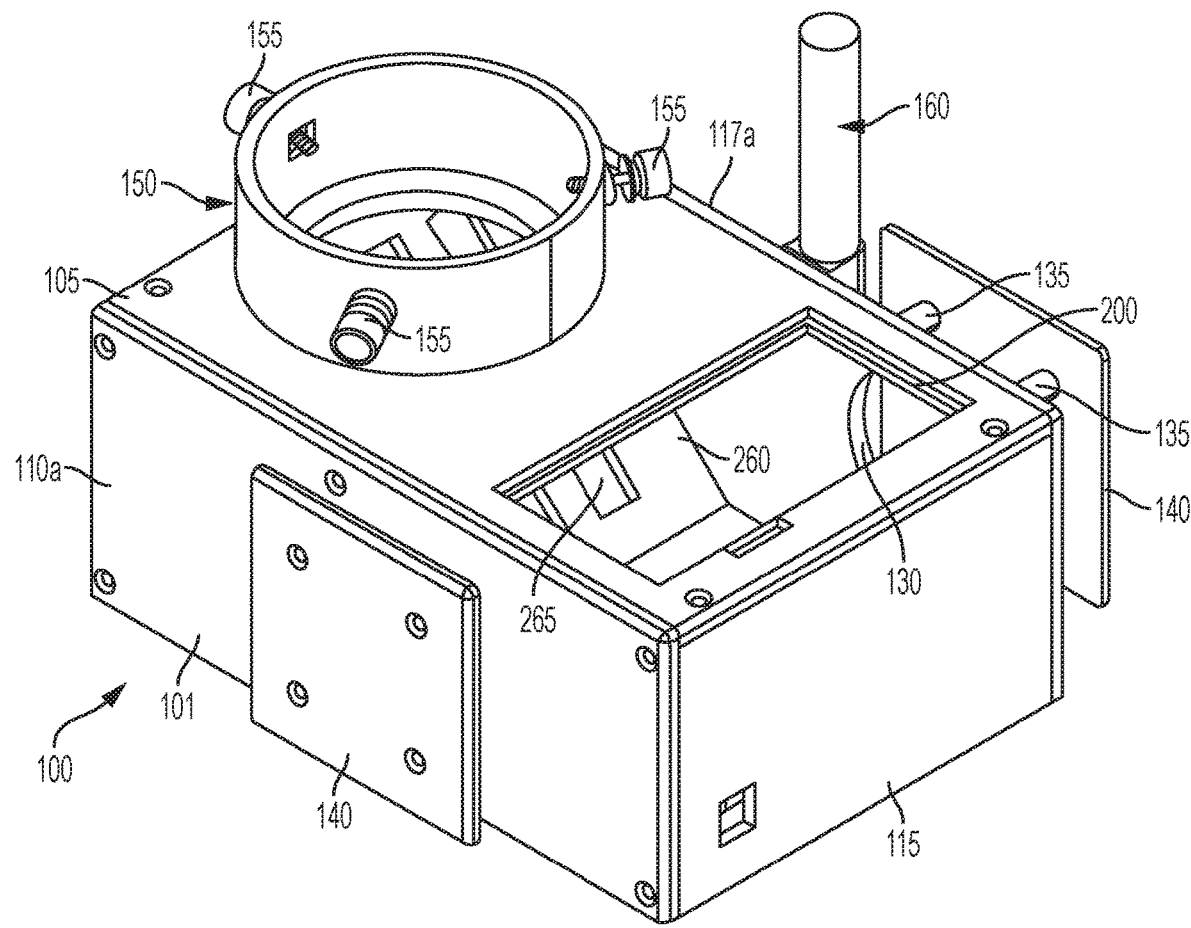
FIG. 1 is a front elevated view of one embodiment of an assembly of this invention for conducting photochemical reactions.

A description of example embodiments of the invention follows.

As used herein, photochemical reactions refer to chemical reactions where absorption of light initiates or influences the rate of reaction. Typically, a molecule or intermediate absorbs a photon of light, which promotes an electron to a higher energetic state. Typically, the electron in the highest occupied molecular orbital (HOMO) is promoted to a higher energy state. Frequently, but not always, the orbital receiving the electron is the lowest unoccupied molecular orbital (LUMO). The molecule that has absorbed a photon of light is said to be in an excited electronic state. Photochemical reactions also includes photoredox catalysis, which relies on the ability of the excited photocatalyst to act as both an oxidant and a reductant in its excited state, thereby allowing energy transfer from the excited molecule to facilitate catalysis of chemical reactions.

Described herein are assemblies for performing photochemical reactions. In some embodiments, multiple reaction vials can be irradiated with light simultaneously, thereby allowing a multiple photochemical reactions to be investigated simultaneously. In some embodiments, vials of different sizes can be used. The light source emits light into the assembly, and the light is reflected toward the reaction vials by one or more mirrors. The assembly can be set up on a standard stirring plate to allow for magnetic stirring of the reaction conditions. In some embodiments, the assembly includes a handle, which can be secured to a standard laboratory clamp and stand. The interior of the cavity can be cooled by allowing a fluid, such as a gas or liquid, to flow through the cavity. In some embodiments, the fluid is a gas, such as air, and a fan can facilitate flow of the gas through inlet and outlet ports. In other embodiments, the fluid is a liquid, such as water, and the inlet and outlet ports are nozzles. In some embodiments, the assembly can receive multiple light sources. In some embodiments, the assembly can have multiple openings for receiving a removable holder, which is capable of holding one or more reaction vials.

An important feature of assemblies described herein is that the source of light is separated from and exterior to the interior cavity. Sources of light, particularly UV light, tend to generate a substantial amount of heat. If the light source is within the chamber, then the temperature of the chamber can increase during the course of a reaction, which may be several hours (e.g., 18-24 hours). Chemical reactions are often sensitive to temperature. When performing reactions, it is often preferred to maintain the reaction vials at a constant temperature, frequently room temperature, in order to minimize the effects of temperature changes on reaction rates. While ensuring appropriate separation of the light source and reaction chamber, it can also be important to ensure that the light irradiates the reaction vials as uniformly as possible.

FIG. 1 is an embodiment of an assembly 100 for performing photochemical reactions. The assembly 100 for performing photochemical reactions includes a housing 101. In this particular embodiment, the housing 101 has a top face 105, side faces (110a, 115), and a bottom face (not shown). The top face 105 has an opening 200 for receiving a removable holder (210a, 210b, 210c, 210d) (FIG. 4) for reaction vials.

Figure 2:
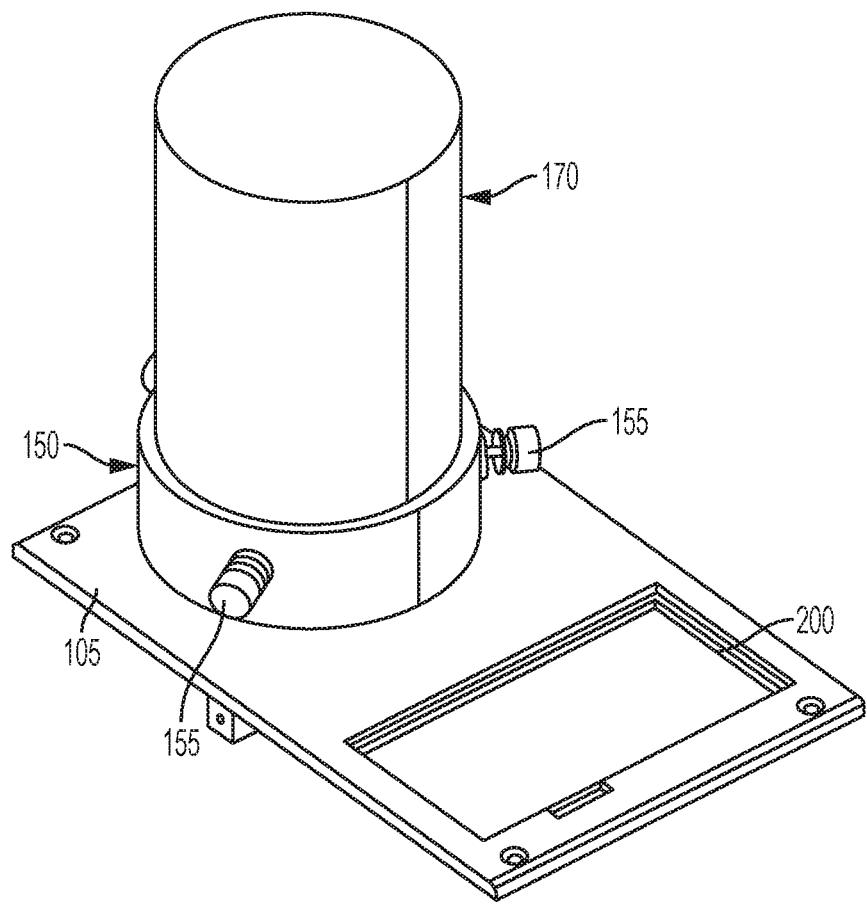
FIG. 2 is a front elevated view of one embodiment of a top face of a housing of this invention.

Top face 105 has an adaptor 150 for receiving a light source 170 (see FIG. 2). The adaptor ensures that the light source 170 is securely attached to the housing 101. In the embodiment of FIG. 1, three screws 155 can be tightened to ensure a secure fit. Other embodiments for ensuring a secure fit are also possible, such as a press-fit arrangement. As illustrated, adaptor 150 is cylindrical, but other geometries are permissible and the adaptor shape can be changed to accommodate different light sources. As shown in FIG. 2, top face 105 is removable from the remainder of housing 101. In one embodiment, light source 170 can emit ultraviolet (UV) light.

The housing is adapted to permit entry and exit of a fluid, which can heat or cool the reaction vials as desired. In the embodiment of FIG. 1, opposing side faces 110a and 117a have ports to permit entry and exit of a gas, such as air. In this embodiment, side face 117a has an opening 130 that permits entry of a gas, and side face 110a has an opening (not shown) behind cover 140 that permits exit of a gas. Behind one of the covers 140 is a fan 145 (see FIG. 6B) that facilitates flow of the gas through the interior of the housing 101. Side face 117a also has a cover 140 that is offset from opening 130 by short pegs. The cover 140 on side face 117a permits flow of gas, while also restricting or reducing light from escaping via opening 130. Frequently, UV light is used for photochemical reactions, and restricting the light from escaping protects the eyes of the person using the assembly.

Figure 4:
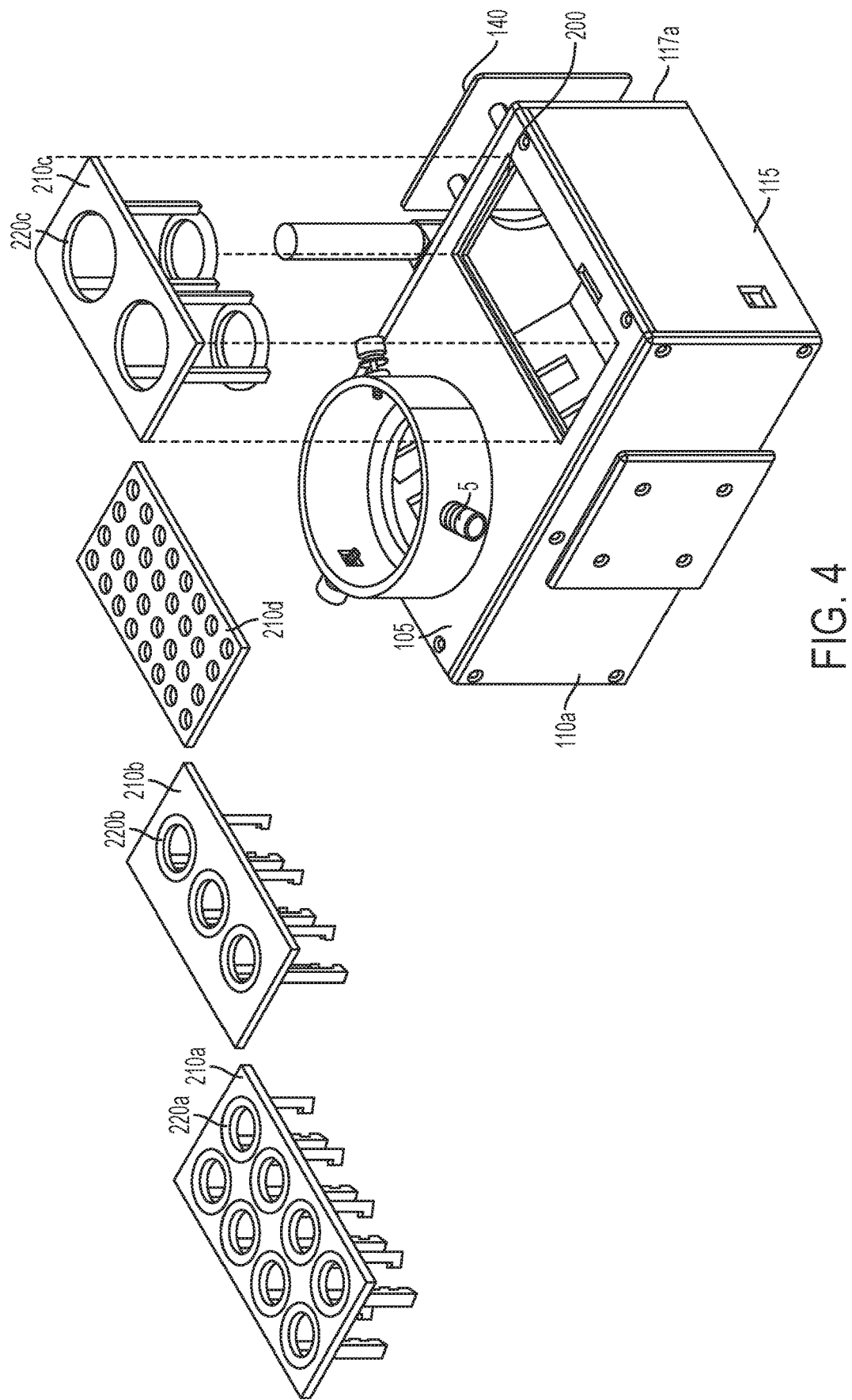
FIG. 4 is a front elevated view of an embodiment for an assembly of this invention for conducting photochemical reactions, along with several removable holders for reaction vials.

As shown in FIG. 4, different removable holders 210 can be adapted to receive reaction vials of different sizes. For example, removable holder 210a is adapted to receive eight reaction vials. In some embodiments, removable holder 210a is adapted to receive eight reaction vials, each of which holds 1 mL. Removable holder 210b is adapted to receive three reaction vials. In some embodiments, removable holder 210b is adapted to receive three reaction vials, each of which holds 2 mL. Removable holder 210c is adapted to receive two reaction vials. In some embodiments, removable holder 210b is adapted to receive two reaction vials, each of which holds 10 mL. Removable holder 210d is adapted to receive 32 reaction vials. In some embodiments, removable holder 210d is adapted to receive 32 reaction vials, each of which holds 0.1 mL. In some embodiments, a removable holder 210 can hold a single reaction vial (not shown). Removable holders 210 can include an insert 220 that supports the reaction vials. For example removable holder 210 includes inserts 220a, and removable holder 210b includes inserts 220b. As illustrated, removable holders 210c and 210d do not include inserts, but such inserts can be included. FIG. 5B is an enlarged view of an insert 220a with a reaction vial 230a therein. FIG. 5C is an enlarged view of an insert 220a.

In some embodiments, a handle 160 is affixed to the housing 101. As illustrated in FIG. 1, handle 160 is affixed to side face 117a. However, handle 160 can be affixed to any convenient location on the housing 101.

FIGS. 3A-B illustrate the interior cavity 240 of the housing 101. Within the interior cavity 240 is one or more mirrors 180a-d, typically a plurality of mirrors 180a-d. As illustrated in FIGS. 3A-B, light shines downward from light source 170, through adaptor 150, and into the interior cavity 240 of housing 101. The light can reflect off of one or mirrors so that it is incident upon one or more reaction vessels 230. As illustrated, light reflects off mirror 180a towards mirror 180c toward one or more reaction vessels 230. As illustrated, mirror 180a is positioned such that a face of the mirror extends from a top corner of the interior cavity towards the bottom of the housing. The mirror is positioned such that the angle $\theta_1$ is an acute angle relative to the side face 113a. As illustrated, the mirrors are positioned such that $\theta_1$ is approximately 45° angles and $\theta_2$ is approximately 45°, though a wide variety of other angles that provide sufficient reflection within the interior cavity are suitable. The mirrors are positioned so that they reflect light toward the reaction vials. Preferably, the interior of the housing 101 is fully covered with mirrors.

Since the light source is not within the interior cavity, heat from the light source is more readily dissipated. As a result, temperature fluctuations of the reaction vessels can be reduced or minimized. Additionally, the assembly can be set up on a standard stirring plate, thereby allowing magnetic stirring within the reaction vessels.

Figure 6B:
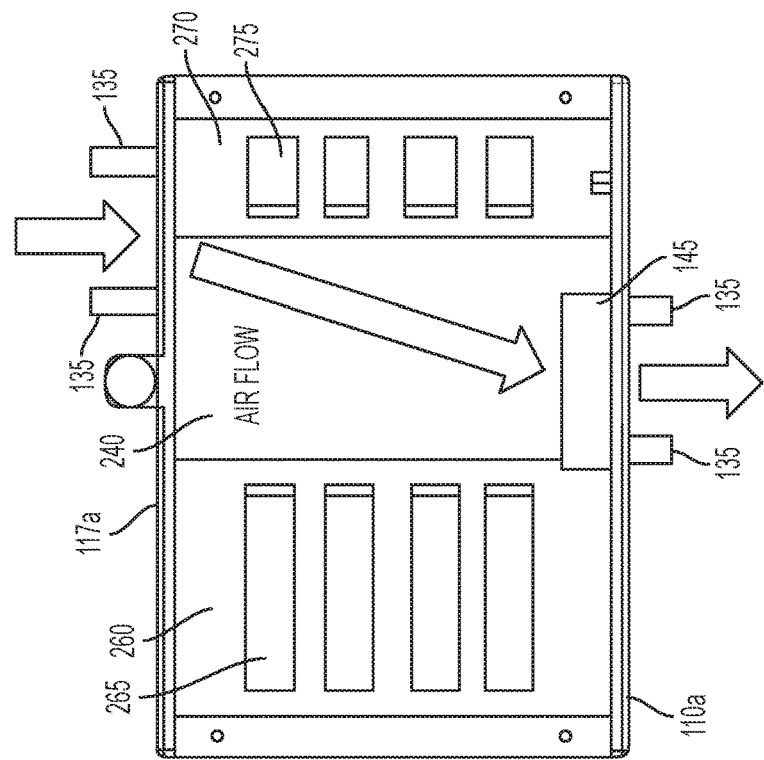
FIG. 6B is a top view of the interior cavity of an embodiment of an assembly of this invention.
Figure 6A:
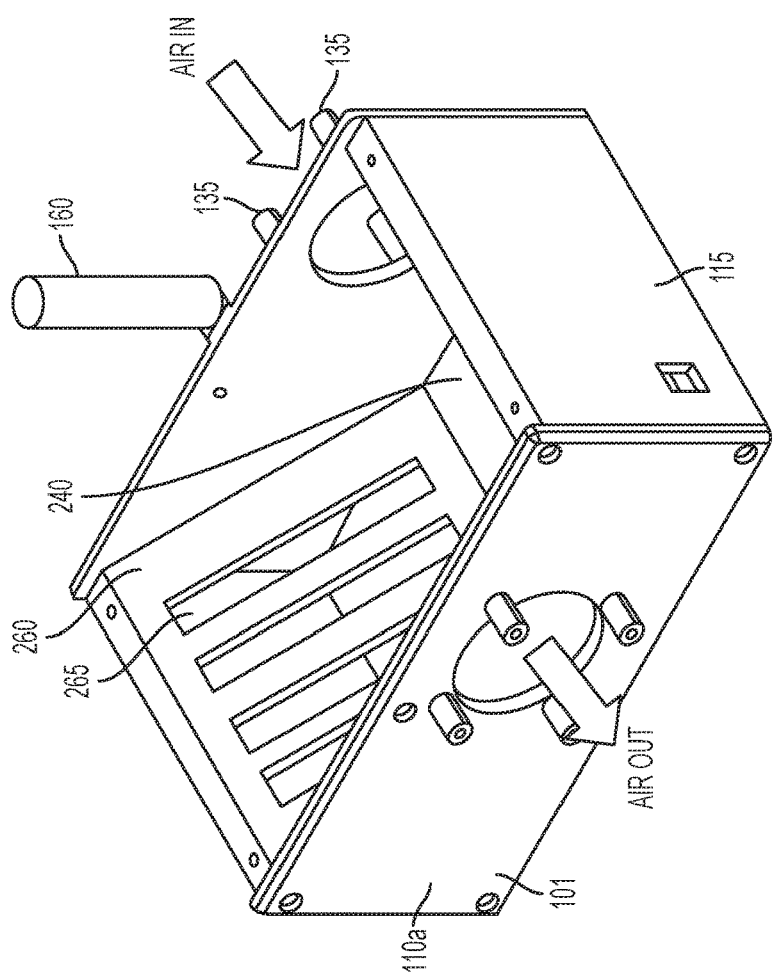
FIG. 6A is a front elevated view of the interior cavity of an embodiment of an assembly, which shows airflow through the assembly.

FIGS. 6A and 6B illustrate alternative views of the interior cavity 240 of the housing 101. As illustrated, supporting frame 260 includes slots 265, and supporting frame 270 includes slots 275. The frame serves as a support for mirrors, which are affixed to the frame. Including slots (265, 275) in the frames (260 and 270) reduces the amount of material in the product, which can reduce manufacturing costs.

Figure 7A:
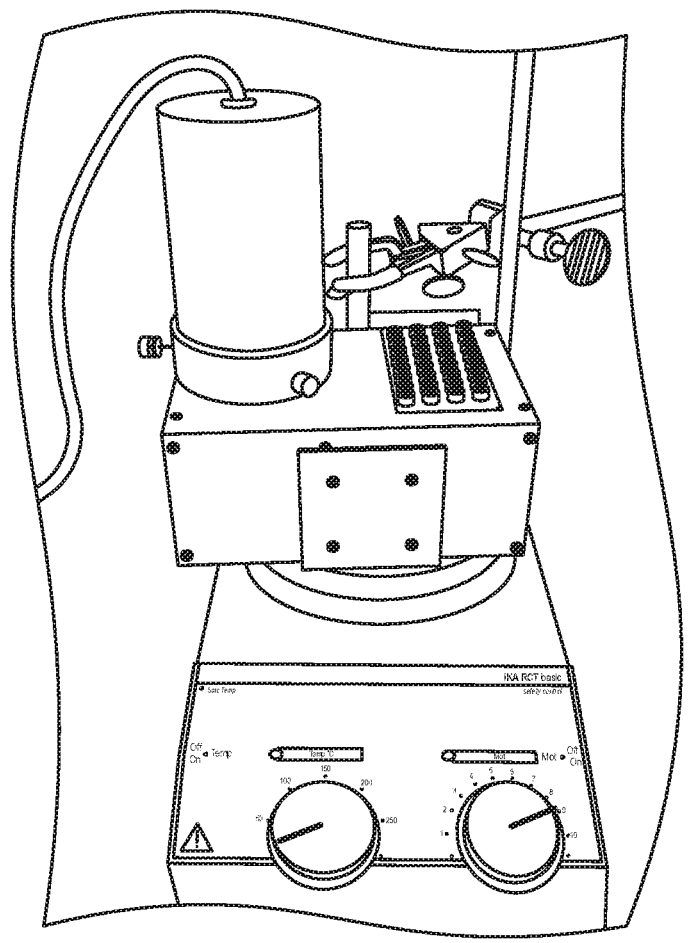
FIGS. 7A-C are schematics of an embodiment of an assembly of this invention for performing photochemical reactions.
Figure 7B:
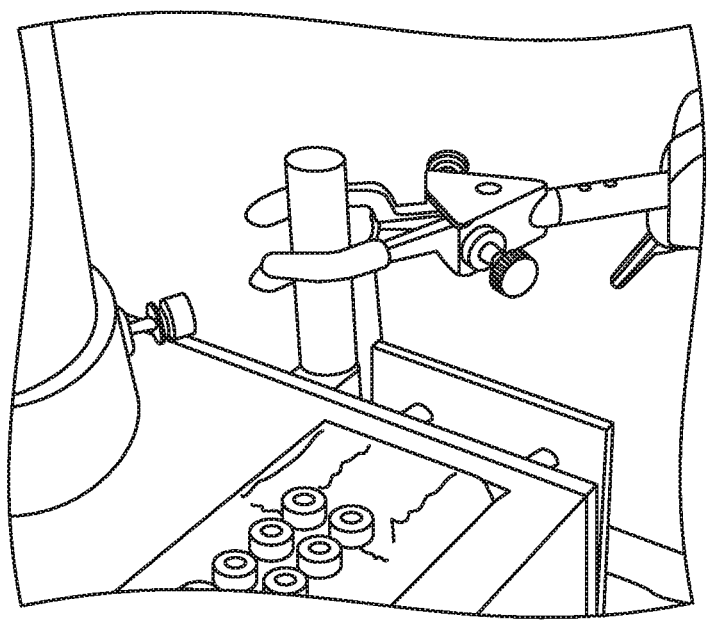
Figure 7C:
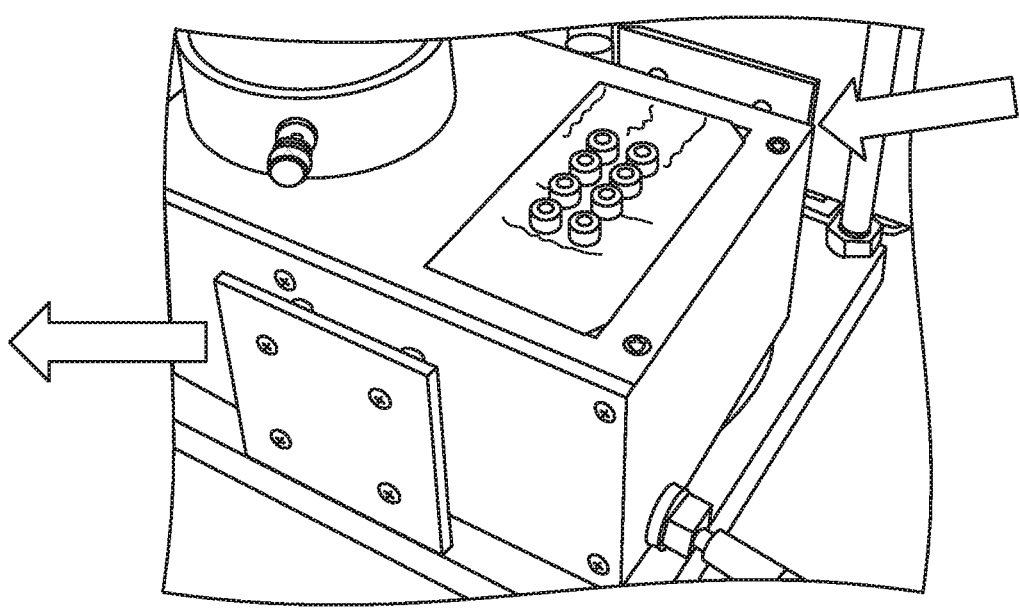
Figure 8A:
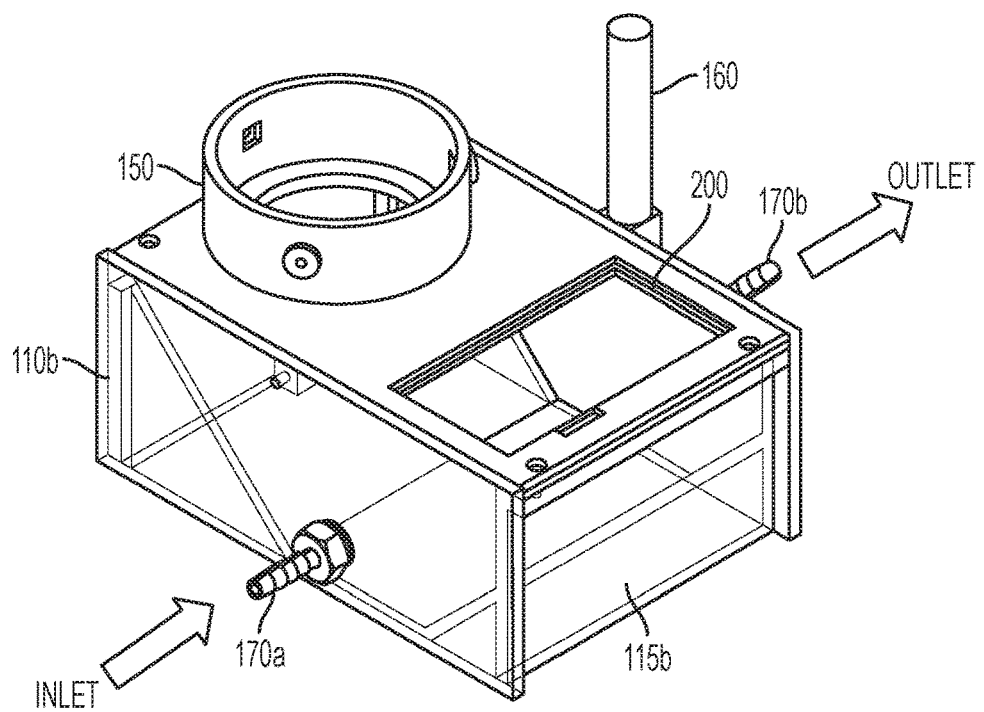
FIG. 8A-B are front elevated views of an embodiment for performing chemical reactions. In the embodiment of FIG. 8A-B, the interior cavity is cooled by a liquid.
Figure 8B:
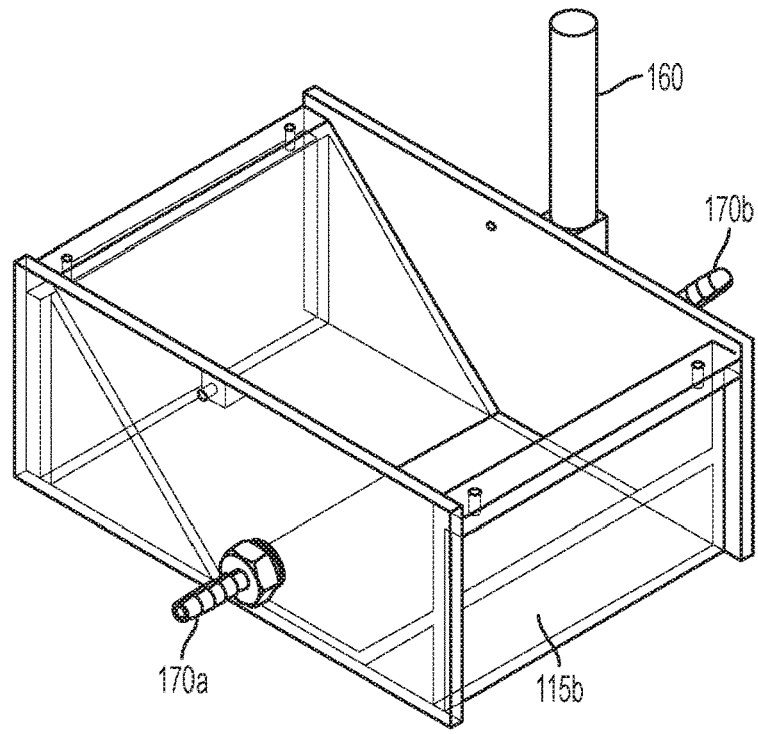
Figure 10A:
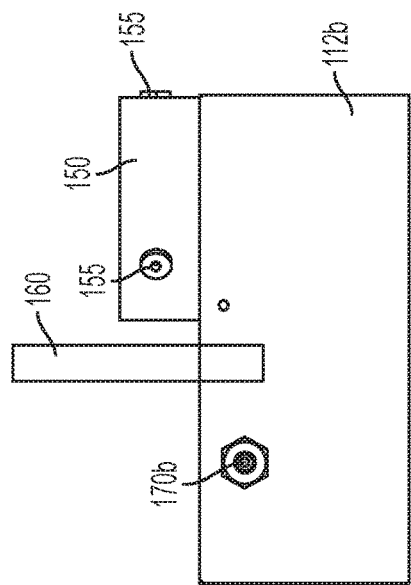
FIGS. 10A-C are three side views of the embodiment of FIGS. 8A-B.
Figure 10B:
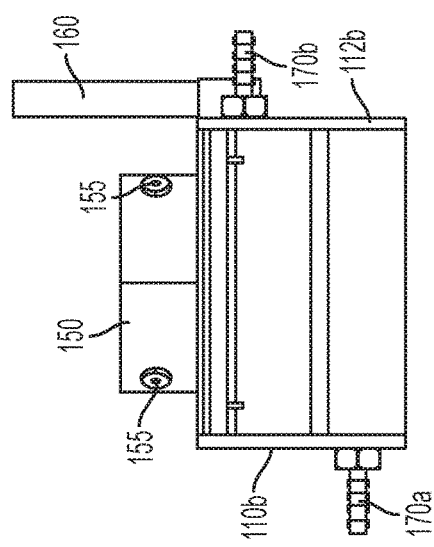
Figure 10C:
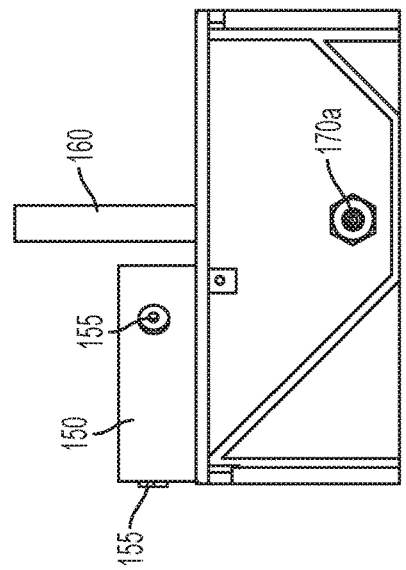

FIGS. 7A-C are schematics of an embodiment of an assembly of this invention for performing photochemical reactions. FIG. 7A shows the assembly on a standard laboratory stir plate. The assembly is secured by clamping the handle with a standard three-prong laboratory clamp to a ring stand. FIG. 7B is a schematic showing a magnified view of the three-prong laboratory clamp securing the handle of the assembly. Also illustrated is a plurality of reaction vials seated in the removable holder. FIG. 7C is another schematic of an assembly, with arrows indicating the flow of gas in and out of the assembly.

In another embodiment, shown in FIGS. 8A-B, 9, and 10A-C, the interior cavity is cooled by a liquid instead of a gas. Side faces 110b and 117b have nozzles (170a, 170b) for permitting inlet and outlet of a liquid, such as water, which cools the interior chamber and the reaction vessels. Typically, nozzle 170a is positioned lower than nozzle 170b so that as liquid enters the interior 250, the liquid fills up the chamber and flows out through nozzle 170b, which is at a higher position. In FIG. 9, an outline of the liquid level 180 indicates that the chamber can be filled so that the water contacts the reaction vessels 230. As illustrated, nozzles 170a and 170b are also offset relative to side face 115b of the reaction chamber.

The liquid can be circulated by a pump with tubing attached to nozzles 170a, 170b. In one embodiment, the cooling loop includes a chiller that removes heat from the liquid. In another embodiment, the cooling loop includes a heater that adds heat to the liquid. For example, most chemical reactions proceed at faster rates as temperature increases. Some reactions need to be conducted at a temperature greater than room temperature in order for the reaction to proceed within a reasonable time period. Accordingly, a heater unit can be advantageous for controlling temperature and heating the reaction vials to a temperature greater than room temperature. Some embodiments have a device that can function as either a chiller or a heater. A recirculation loop with a chiller unit or heater unit allows the reactions to be performed at desired temperatures.

Figure 14:
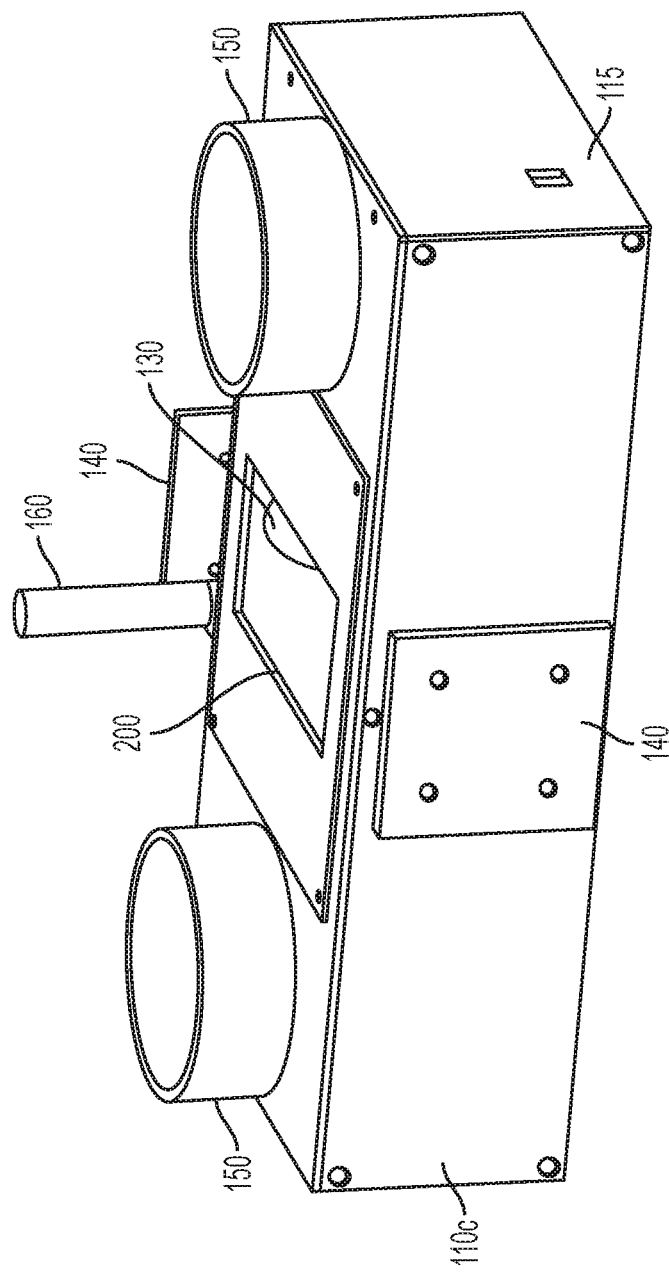
FIG. 14 is an embodiment of an assembly of the invention having two adaptors to receive a light source and one opening for receiving a removable holder.
Figure 15:
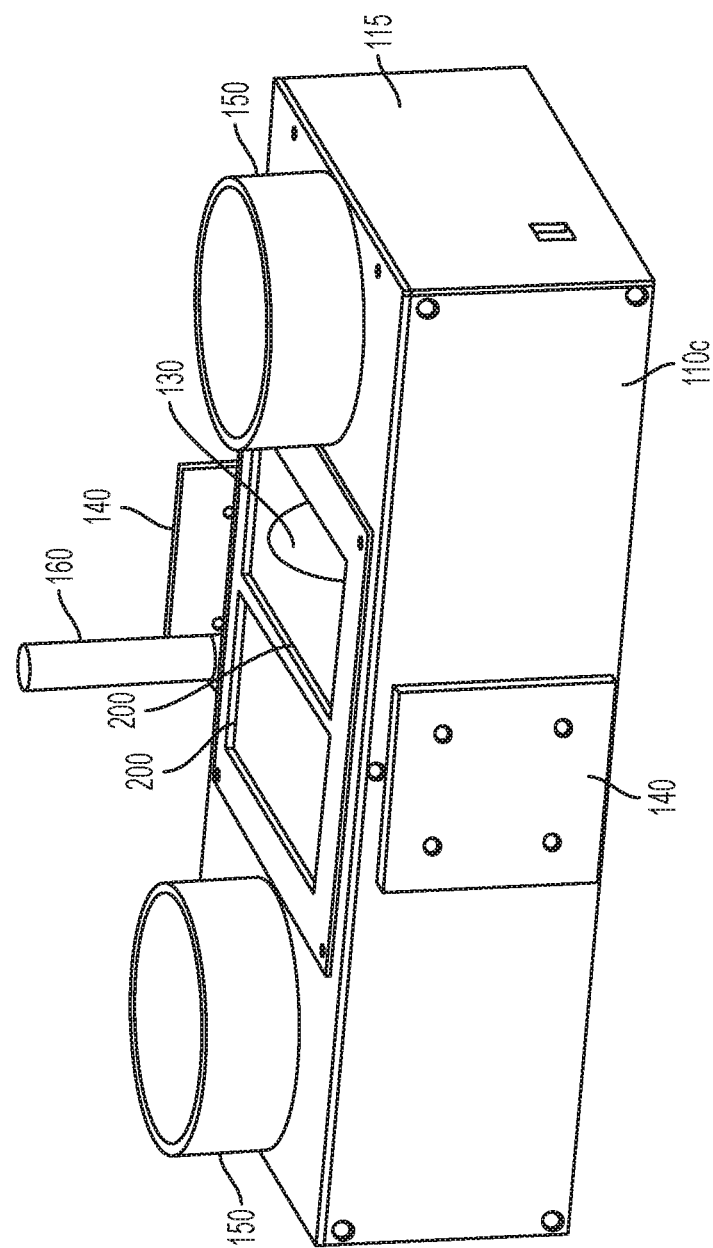
FIG. 15 is an embodiment of an assembly of the invention having two adaptors to receive a light source and two openings for receiving a removable holder.

Two other embodiments of assemblies of this invention are shown in FIGS. 14 and 15. In the embodiment of FIG. 14, the assembly has two adaptors 150 to receive a light source and one opening 200 for receiving a removable holder. In the embodiment of FIG. 15, the assembly has two adaptors 150 to receive a light source and two openings 200 for receiving a removable holder. These assemblies function according to similar principles as others described herein. The embodiments of FIGS. 14 and 15 have openings behind covers 140 that permits inlet and outlet of a gas. A handle 160 is affixed to the housing. In the embodiment of FIGS. 14 and 15, side face 110c is longer than side face 110a (of FIG. 1).

In FIGS. 14 and 15 light shines downward from two light sources, through each adaptor 150, and into an interior cavity of the housing. Within the interior cavity is one or more mirrors, typically a plurality of mirrors, positioned such that light reflects off the one or more mirrors and then is incident upon one or more reaction vessels, which are supported by a removable reaction holder seated within opening 200.

The embodiments of FIGS. 14 and 15 permit a gas to flow through openings behind covers 140 in a manner similar to the embodiment of FIG. 1. The embodiments of FIGS. 14 and 15 can be adapted to permit the interior cavity to be cooled or heated by a liquid, as in FIGS. 8A-B, 9, and 10A-C, by providing appropriate nozzles for inlet and outlet of a liquid.

Preferably, the assembly for performing photochemical reactions is formed of a polymeric (e.g., plastic) material. When formed of a polymeric material, the assembly can be placed on a magnetic stir plate, which can facilitate stirring the reactions.

A wide variety of photochemical reactions can be conducted in the assemblies described herein. By way of example, three examples of photochemical reactions are described.

EXEMPLIFICATION

Example 1: Light Distribution Test

Figure 11:
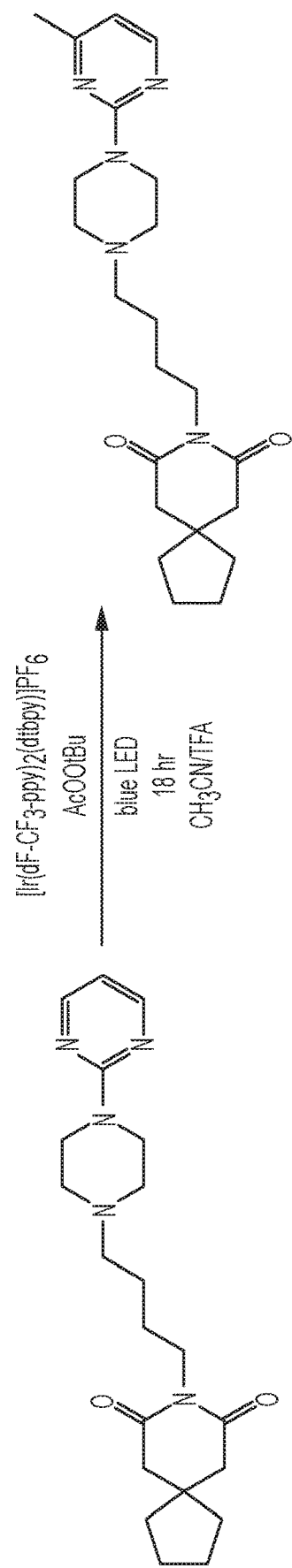
FIG. 11 is a reaction for a light distribution test.
Figure 12:
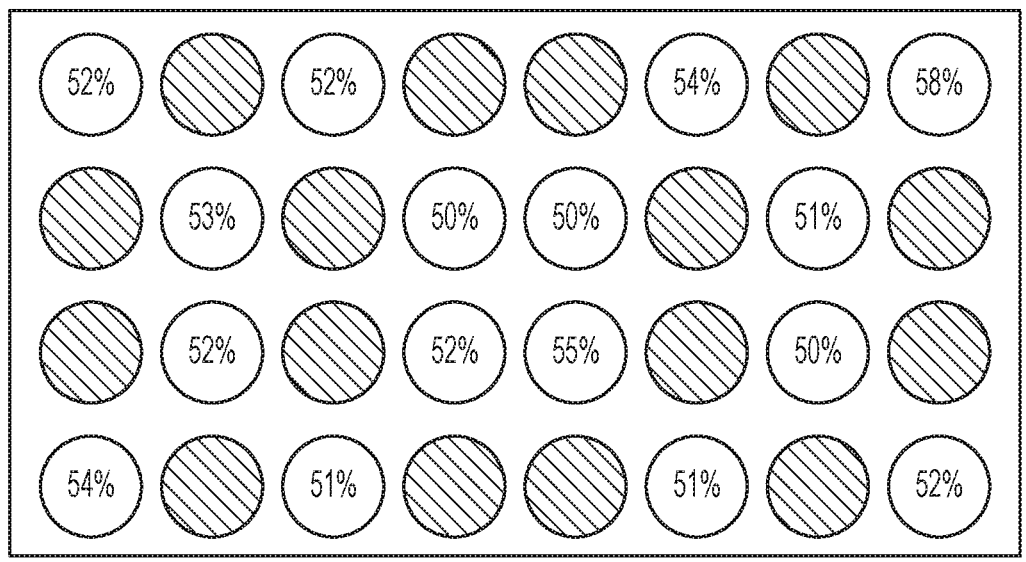
FIG. 12 is an illustration of the results of a light distribution test.

A light distribution test was conducted with an assembly, similar to FIG. 1, and appropriate reactants for performing photomethylation of buspirone. A removable holder capable of holding 32 vials was used. Sixteen vials, each capable of holding 0.3 mL, were randomly distributed in the removable holder. Each reaction vial contained Ir(dF-CF$_3$-ppy)$_2$(dtbpy)[PF$_6$] (0.1 µmol), tert-butylperacetate solution (12.5 µmol) and a stir bar sealed under inert atmosphere. To each vial was added 50 µl of 0.05 M buspirone solution in 1:1 trifluoroacetic acid/acetonitrile sparged with a nitrogen stream. The reaction holder was placed in the assembly and irradiated with a Kessil 34 W blue LED for 18 hours. In Trial #1, 53% (+/−2%) conversion according to the reaction depicted in FIG. 11 was observed by LC-UV. FIG. 12 is an illustration depicting the percent conversion at each location within the removable holder in Trial #1. As illustrated, the side labeled as "front" is the side closer to the adaptor for receiving the light source. In Trial #2, 16 reaction vials were randomly distributed, and an average conversion of 56% (+/−2%) to the mono-methylated product was observed.

Example 2: Decarboxylative Arylation of α-Amino Acids

Figure 13:
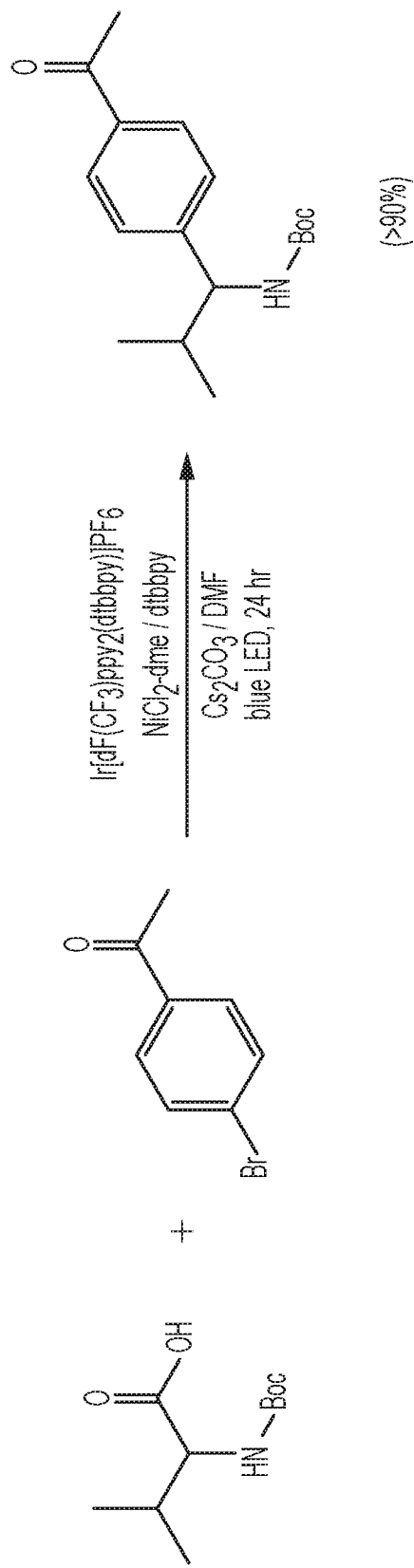
FIG. 13 is a reaction for a decarboxylative arylation of α-amino acids test.

A light distribution test was conducted with an assembly, similar to FIG. 1, and appropriate reactants. In duplicate in a 4-ml vial equipped with a TEFLON septa and 2×7 mm stir bar, were weighed NiCl$_2$-dme (2.2 mg, 10 µmol, 0.1 mol %), dtbbpy (2.68 mg, 10 µmol, 0.1 mol %), Ir(dF-CF3-ppy)$_2$(dtbpy) (2.24 mg, 2 µmol, 0.02 mol %), and Cs$_2$CO$_3$ (97.8 mg, 300 µmol, 3 equiv.). To each vial was added a 2.0 ml solution in DMF containing Boc-Val-OH (10.85 mg, 100 µmol, 1 equiv.) and 4-bromoacetophenone (9.95 mg, 100 µmol, 1 equiv.). The solution was sparged with nitrogen via submerged needle for 5 minutes and vial was placed in a removable holder capable of holding eight reaction vials. The reaction holder was placed in the assembly and irradiated with a Kessil 34 W blue LED for 24 hrs. Reaction progress was monitored by liquid chromatography-mass spectrometry (LC-MS). After 24 hours, conversion was greater than 90%. No additional product was observed at 48 hrs. FIG. 13 shows the reaction schematic.

Example 3: Photoredox Cross-Coupling Reaction

Figure 17:
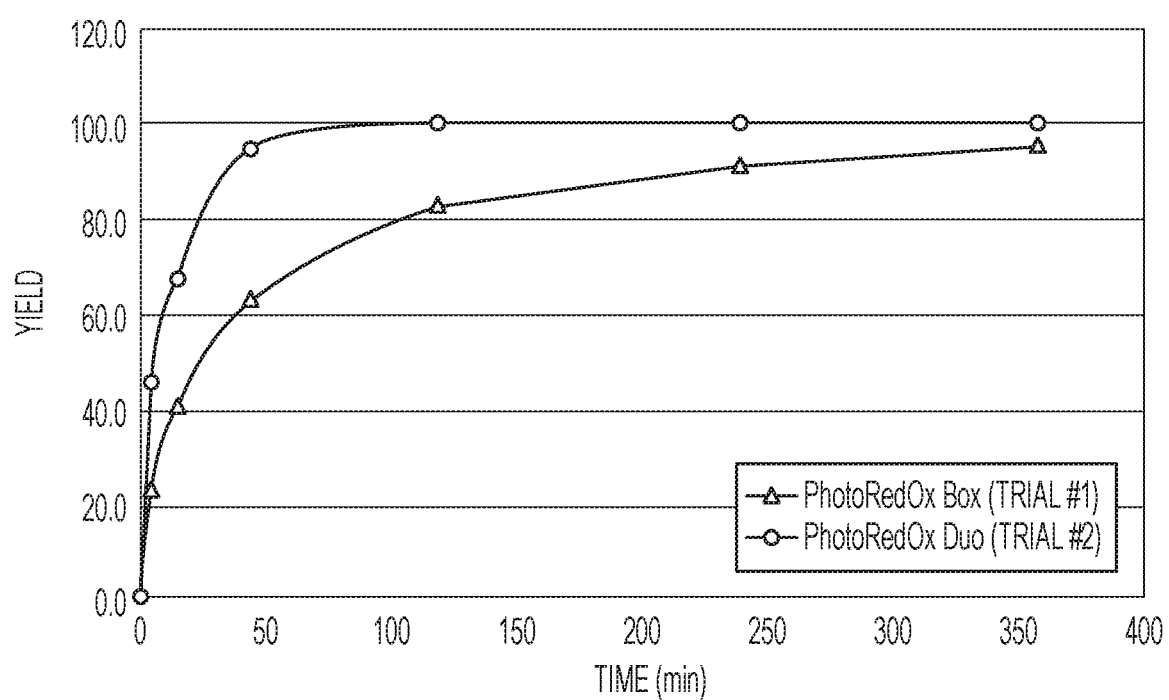
FIG. 17 is a graph of the reaction yield over time for a photoredox cross-coupling reaction test with the assembly embodiments of FIGS. 14 and 15.

In duplicate in a 4-ml vial equipped with a TEFLON septa and 2×7 mm stir bar, were weighed 4-bromoacetophenone (4.95 mg, 25 µmol) and potassium benzyltrifluoroborate (4.50 mg, 25 µmol, 1 equiv.). To this vial was added a 1.0 ml solution in DMA containing NiCl$_2$-dme (1.1 mg, 5 µmol, 0.1 mol %), dtbbpy (1.3 mg, 5 µmol, 0.1 mol %) and Ir(dF-CF$_3$-ppy)$_2$(dtbpy) (1.12 mg, 1 µmol, 0.02 mol %) followed by addition of 2,6-lutidine (17.5 µl, 150 µmol, 6 equiv.). The solution was sparged with nitrogen via submerged needle for 5 minutes and vial was placed in the assemblies. For Trial #1, the assembly was an embodiment having two adaptors for receiving a light source and one opening for receiving a removable holder (similar to FIG. 14). For Trial #2, the assembly was an embodiment having two adaptors for receiving a light source and two openings for receiving a removable holder (similar to FIG. 15). In Trials #1 and #2, the assembly was irradiated with one (Trial #1) or two (Trial #2) Kessil 34 W blue LED. The reaction yield was measured at 0, 5, 15, 45, 120, 240, 360 and 1440 minutes. In Trial #1, 96% yield was measured at 360 minutes. In Trial #2, 95% yield was measured at 45 minutes. FIG. 17 is a graph of the reaction yield over time.

INCORPORATION BY REFERENCE AND EQUIVALENTS

The relevant teachings of all patents, published applications and references cited herein are incorporated by reference.

While example embodiments have been particularly shown and described, it will be understood by those skilled in the art that various changes in form and details may be made therein without departing from the scope of the embodiments encompassed by the appended claims.

What is claimed is:

1. An assembly for performing one or more photochemical reactions, the assembly comprising:
   a housing defining an interior cavity having positioned therein one or more mirrors to reflect light from a first light source towards one or more reaction vials, wherein the housing comprises:
   i) a first opening for receiving a first removable holder, the first removable holder capable of holding the one or more reaction vials;
   ii) a first adaptor for receiving the first light source, wherein the first light source is exterior to the housing to dissipate heat generated by the first light source external to the assembly; and
   iii) ports for entry and exit of a fluid for adjusting the temperature of the reaction vials.

2. The assembly of claim 1, further comprising a handle affixed to the housing.

3. The assembly of claim 1, wherein a top face of the housing is removable.

4. The assembly of claim 1, wherein one or more screws couple the first light source with the first adaptor for receiving the first light source.

5. The assembly of claim 1, wherein different removable holders for reaction vials are adapted to receive reactions vials of different sizes.

6. The assembly of claim 1, wherein the first removable holder for reaction vials has openings to receive 2, 3, 8, or 32 reaction vials.

7. The assembly of claim 1, wherein the housing comprises a second adaptor for receiving a second light source, wherein the second light source is exterior to the housing to dissipate heat generated by the second light source external to the assembly.

8. The assembly of claim 1, wherein the housing comprises a second opening for receiving a second removable holder, the second removable holder capable of holding the one or more reaction vials.

9. The assembly of claim 1, wherein the housing comprises a second adaptor for receiving a second light source, wherein the second light source is exterior to the housing to dissipate heat generated by the second light source external to the assembly; and a second opening for receiving a second removable holder, the second removable holder capable of holding the one or more reaction vials.

10. The assembly of claim 1, wherein:
a) the one or more mirrors comprises a first mirror positioned such that a face of the first mirror extends from a top corner of the interior cavity towards a bottom face of the housing, and at an acute angle relative to a side wall, such that the first mirror reflects light toward an opposing side wall.

11. The assembly of claim 1, wherein the ports are openings to permit a gas to flow into and out of the interior cavity.

12. The assembly of claim 11, further comprising a fan at one of the ports.

13. The assembly of claim 11, further comprising a cover parallel to and offset from one of the ports.

14. The assembly of claim 1, wherein the ports are nozzles to permit a liquid to flow into and out of the interior cavity.

\* \* \* \* \*